United States Patent [19]

Engebrecht et al.

[11] Patent Number: 5,132,436

[45] Date of Patent: Jul. 21, 1992

[54] INTERMEDIATES FOR MAKING 14-CROWN-4-ETHER DERIVATIVES

[75] Inventors: Ronald H. Engebrecht, Victor; Thomas R. Welter, Webster, both of N.Y.

[73] Assignee: Eastman Kodak Company, Rochester, N.Y.

[21] Appl. No.: 706,431

[22] Filed: May 28, 1991

[51] Int. Cl.$^5$ .......................................... C07D 323/00
[52] U.S. Cl. .................................... 549/353
[58] Field of Search ......................... 549/353

[56] References Cited

U.S. PATENT DOCUMENTS

| | | | |
|---|---|---|---|
| 4,367,072 | 1/1983 | Vogtle et al. | 436/501 |
| 4,645,744 | 2/1987 | Charlton et al. | 436/74 |
| 4,659,815 | 4/1987 | Pacey et al. | 540/467 |
| 4,734,376 | 3/1988 | Pacey et al. | 436/79 |
| 4,762,799 | 8/1988 | Seitz et al. | 436/79 |

FOREIGN PATENT DOCUMENTS

| | | |
|---|---|---|
| 58-046517B | 10/1983 | Japan. |
| 0202875 | 10/1985 | Japan. |
| 1260078 | 11/1986 | Japan. |
| 2033170 | 2/1987 | Japan. |
| 2056485 | 3/1987 | Japan. |
| 63-201566A | 8/1988 | Japan. |

Primary Examiner—Jane T. Fan
Assistant Examiner—Melia A. Owens
Attorney, Agent, or Firm—John R. Everett

[57] ABSTRACT

Intermediate compounds for the preparation of useful 14-crown-4-ether derivatives are presented. The intermediates have the structure:

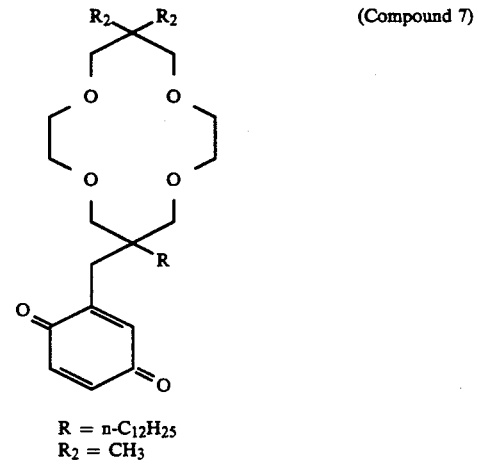

(Compound 7)

$R = n\text{-}C_{12}H_{25}$
$R_2 = CH_3$ wherein R represents $CH_3$, $n\text{-}C_{12}H_{25}$ and $CH_2C_6H_5$; and $R_2$ represents $CH_3$, and $n\text{-}C_7H_{15}$.

2 Claims, No Drawings

INTERMEDIATES FOR MAKING 14-CROWN-4-ETHER DERIVATIVES

FIELD OF THE INVENTION

This invention relates to the field of clinical chemistry, particularly intermediate compounds for making 14-Crown-4-Ethers that are useful in lithium assays, and a method of making such intermediate compounds.

BACKGROUND

Lithium in the form of lithium carbonate is administered to manic-depressive patients. The therapeutic range of lithium ion in plasma is quite narrow, namely, 0.8 to 1.2 mM. It is important to monitor the lithium level in such patients because of the toxic side effects that appear when the lithium level in blood exceeds the recommended level.

Lithium is determined quantitatively using solution assays and ion-selective electrodes. Dyes, such as 14-Crown-4-ether derivatives are known for use in such assays. Japanese Kokai 62/72683 (1985) discloses a class of such dyes that act as colorometric reagents in extracting lithium and as useful as charge transport carriers for ion-selective electrodes. The problem is that the disclosed dyes cannot be adapted for use in dry analytical elements. It would be desirable to have dyes that could be used to make dry analytical elements for assaying lithium.

SUMMARY OF THE INVENTION

This invention provides new intermediate compounds that are useful in making 14-Crown-4-Ethers that can be adapted for use in dry analytical elements designed for the quantative assay of lithium in serum or other samples suspected of containing lithium. The intermeidiates have the structure:

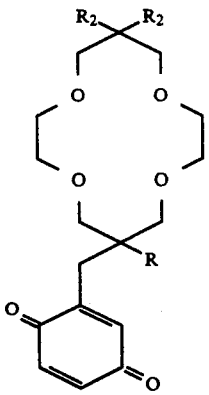

(Compound 7)

R = n-C$_{12}$H$_{25}$
R$_2$ = CH$_3$ wherein R represents CH$_3$, n-C$_{12}$H$_{25}$ and CH$_2$C$_6$H$_5$; and R$_2$ represents CH$_3$, and n-C$_7$H$_{15}$.

The method of making the intermediate compounds comprise the following steps:

a) reducing a 2-substituted-2-[2,5-bis(alkoxy)benzyl]-malonate ester with a strong reducing agent to produce a 2-substituted-2-[2,5-bis(alkoxy)benzyl]-1,3-propanediol, said alkoxy group being benzyloxy or unsubstituted alkoxy of 1 to 10 carbon atoms, b) condensing the 1,3-propanediol of step a) with a 5,5-disubstituted-3,7-dioxanonane-1,9-diylbis(toluene p-sulfonate) to form a 6,13,13-trisubstituted -6-[2,5-bis-(alkoxy)benzyl]-1,4,8,11-tetraoxacyclotetradecane, c) hydrogenating the bis(alkoxy) compound of step b) to the hydroquinone, 6,13,13-trisubstituted6-(2,5-dihydroxybenzyl)-1,4,8,11-tetraoxacyclotetradecane, and d) oxidizing the hydroquinone of step c) to the quinone, 6,13,13-trisubstituted-6-(1,4-cyclohexadiene -3, 6-dione-l-ylmethyl)-1,4,8,11-tetraoxacyclotetradecane.

The above process can be performed by omitting step c) and performing the oxidation step d) on the product of step b) using an oxidizing agent selected from Ag$_2$O$_2$ and cerium ammonium nitrate to directly produce the product of step d).

The following example demonstrates how the above method can be carried out.

EXAMPLE

Preparation Sequence I

The preparation of the diol portion of the compound is shown in Sequence I, infra. A 2,5-dibenzyloxybenzyl chloride, compound 1, is condensed with dimethyl 2-alkylmalonate, compound 2, yielding a 2-substituted-2-[2,5-bis(alkoxy)benzyl]malonate ester compound 3, which is subsequently reduced with a strong reducing agent to produce a 2-substituted-2-[2,5-bis(alkoxy)benzyl]-1,3-propanediol, said alkoxy group being benzyloxy or unsubstituted alkoxy of 1 to 10 carbon atoms, compound 4.

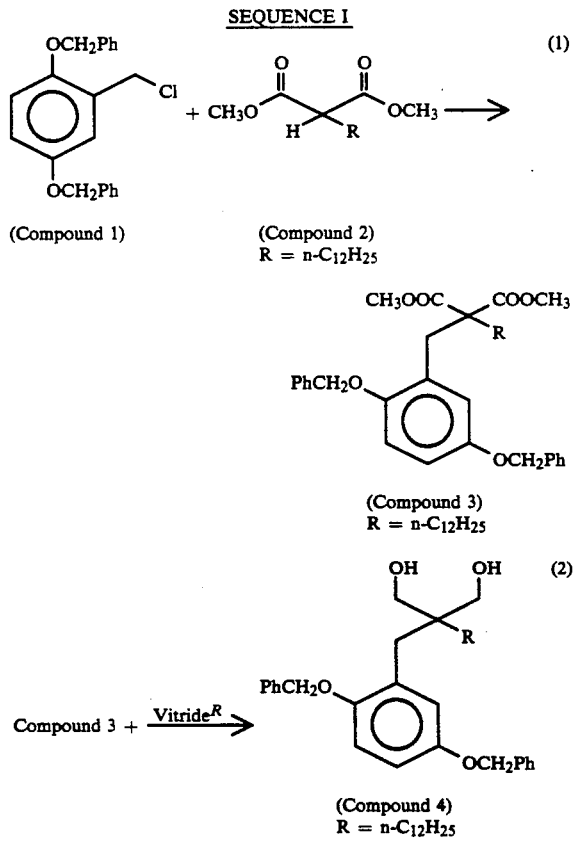

1. Preparation of dimethyl 2-dodecyl-2-[2,5bis(benzyloxy)benzyl]malonate (Compound 3)

A solution of 121.4 g (404.7 mmol) of Compound 2 (dimethyl 2-dodecylmalonate) in 600 mL of dimethylformamide was added to 56.0 g (500 mmol) of potassium tert. butoxide. After 30 minutes the reaction mixture was cooled to 0° C. and 137 g (404.7 mmol) of Compound 1, 2-(chloromethyl)-1,4bis(phenylmethoxy)benzene, was added and the mixture allowed to warm to room temperature for 30 minutes. The mixture was next heated at 60° C. for 90 minutes and an additional 4.5 g of Compound 2 and 4.5 g of potassium tertiary butoxide was added. The reaction mixture was then heated at 60° C. for 10 hours. Removal of the solvent yielded a viscous oil. This oil was partitioned between ethyl acetate and dilute hydrochloric acid, and the organic phase dried over anhydrous sodium sulfate, filtered and concentrated to yield an impure viscous oil (Compound 3). Compound 3 was used as prepared in the next step.

2. Preparation of 2-dodecyl-2-(2,5-di(benzyloxy) benzyl)-1,3-propanediol (Compound 4)

A solution of 302.4 g (502.3 mmol) of Compound 3 in 2 L of toluene was prepared. Then 200 mL of the toluene was distilled off to remove residual water. After cooling to room temperature 303.2 g (1.05 mol) of sodium bis(2-methoxyethoxy)aluminum hydride (Vitride ®) was added and the solution stirred for four hours. The reaction was quenched with 90 mL of water, 0 mL 15% sodium hydroxide and 275 mL water. The toluene phase was isolated and the aqueous phase extracted with 500 mL of toluene. The combined organic extracts were dried over anhydrous sodium sulfate, filtered and the solvent removed. The resulting oily product was triturated with petroleum ether. The resulting solid was filtered and washed with petroleum ether yielding a compound having an $^1$H NMR spectrum consistent with the structure of compound 4 (melting point 64–65° C.).

Preparation Sequence II

The final preparation steps for making the intermediate compound of this invention, compound 7, is shown in Sequence II. The initial ionophore is formed by condensation of 1,3-propanediol, compound 4, with a 5,5-disubstituted-3,7-dioxanonane-1,9-diylbis(toluene p-sulfonate), compound 9, a ditosylate, to form a 6,13,13-trisubstituted-6-[2,5-bis(alkoxy)benzyl]1,4,8,11-tetraoxacyclotetradecane, Compound 5. Compound 9 was prepared according to methods described in the literature. Compound 5 is then hydrogenated to the hydroquinone, 6,13,13-trisubstituted-6-(2,5-dihydroxybenzyl)-1,4,8,11-tetraoxacyclotetradecane, compound 6. Compound 6 is then oxidized to yield 6,13,13-trisubstituted-6-(1,4-cyclohexadiene-3,6-dione1-ylmethyl)-1,4,8,11-tetraoxacyclotetradecane, Compound 7. Compounds 5 and 6 are both novel intermediates.

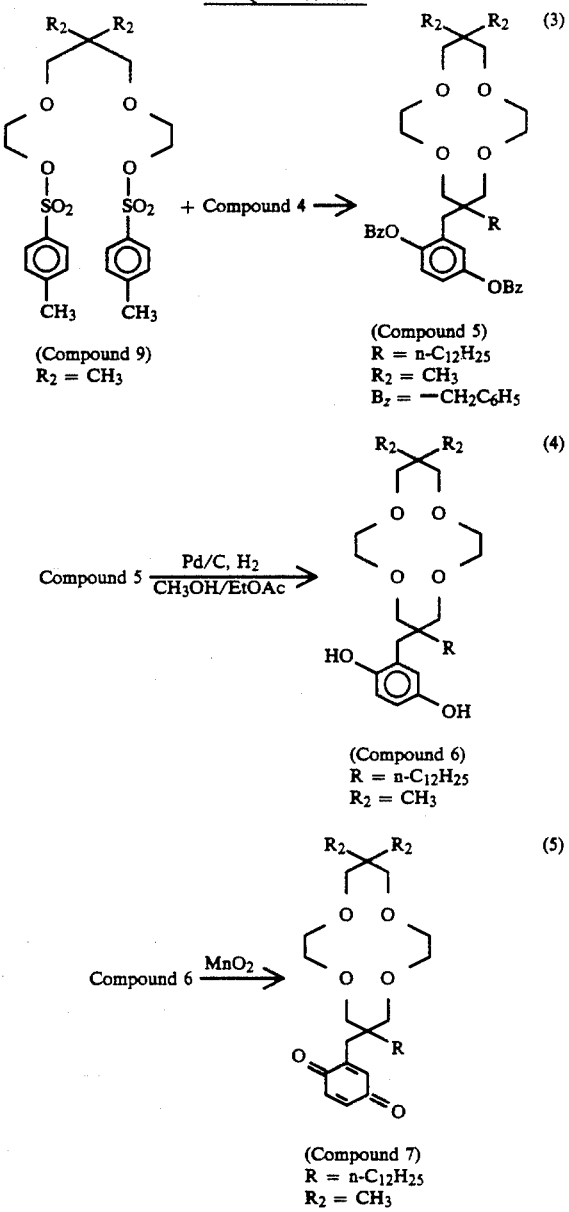

SEQUENCE II (Compound 9)
$R_2 = CH_3$ (Compound 5)
$R = n-C_{12}H_{25}$
$R_2 = CH_3$
$B_z = -CH_2C_6H_5$ (Compound 6)
$R = n-C_{12}H_{25}$
$R_2 = CH_3$ (Compound 7)
$R = n-C_{12}H_{25}$
$R_2 = CH_3$ 3. Preparation of 6-Dodecyl-6-[2,5-di(benzyloxy)-benzyl]-13,13-dimethyl-1,4,8,11-tetraoxacyclotetradecane (Compound 5)

A suspension of 110 g (219.8 mmol) of compound 9, 5,5-dimethyl-3,7-dioxanonane-1,g-diylbis(toluene p-sulfonate), 120 g (219.8 mmol) of compound 4 and 12.2 g (220 mmol) of lithium bromide in 2 L of dry t-pentyl alcohol was reacted with 7.0 g of lithium hydride. After refluxing the reaction mixture for 7 days the solvent was removed and the residue dissolved in a mixture of dichloromethane and dilute hydrochloric acid. The dichloromethane phase was separated, dried over anhydrous magnesium sulfate, filtered and concentrated to a dark oil. The oil was dissolved in 10% dichloromethane/90% petroleum ether and eluted through a silica gel column (600 g) the fractions containing the product (silica gel TLC/CH$_2$Cl$_2$, Rf 0.2) were combined to yield 83.2 g of impure product (Compound 5). 4. Preparation of 6-Dodecyl-6-(2,5-dihydroxybenzyl) -13,13- dimethyl-1,4,8,11-tetraoxacyclotetradecane (Compound 6)

A solution of 15.8 g (22.5 mmol) of Compound 5 in 20 mL of ethyl acetate and 20 mL of methanol was mixed with 0.4 g of palladium-on-carbon in a parr flask under a nitrogen atmosphere. The mixture was reacted at 50–60° C. under 50 psi $H_2$ for 4 hours. After cooling, the product was filtered through Celite diatomaceous earth and the solvent removed to yield 12.7 g of impure product (Compound 6).

5. Preparation of 6-Dodecyl-6-(1,4-cyclohexadiene 3,6-dione-1-ylmethyl)-13,13-dimethyl-1,4,8,11tetraoxacyclotetradecane (Compound 7)

A solution of 67.6 g (129.3 mmol) of Compound 6 in 600 mL of dichloromethane was mixed with 50.6 g (581.9 mmol) of activated manganese dioxide. The heterogeneous mixture was stirred at room temperature for 1 hour. The insolubles were removed by filtration through Celite diatomaceous earth and the solvent removed. The oily residue was triturated with 500 mL of petroleum ether and cooled. The volume of solvent was reduced to ½ and the yellow solid suction filtered and washed with cold pentane.

A first and second fraction of compound 7 was isolated, giving a $^1H$ NMR spectrum consistent with the assigned structure.

The invention has been described in detail with particular reference to preferred embodiments thereof, but it will be understood that variations and modifications can be effected within the spirit and scope of the invention.

What is claimed is:

1. A compound having the structure:

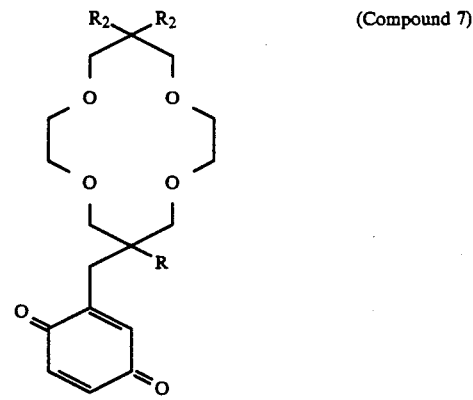

(Compound 7)

wherein R represents $CH_3$, n-$C_{12}H_{25}$ and $CH_2C_6H_5$; and $R_2$ represents $CH_3$, and n-$C_7H_{15}$.

2. The compound of claim 1 wherein R is n-$C_{12}H_{25}$ and $R_2$ is $CH_3$.

* * * * *